United States Patent [19]

Storer et al.

[11] Patent Number: 5,110,926
[45] Date of Patent: May 5, 1992

[54] PROCESS FOR THE PREPARATION OF A CARBOCYCLIC NUCLEOSIDE ANALOGUE

[75] Inventors: Richard Storer, Pinner; Chi L. Mo; John P. Turnbull, both of Greenford, all of England

[73] Assignee: Glaxo Group Limited, London, England

[21] Appl. No.: 553,631

[22] Filed: Jul. 18, 1990

[30] Foreign Application Priority Data

Jul. 19, 1989 [GB] United Kingdom ............... 8916480

[51] Int. Cl.$^5$ .................. C07D 473/18; C07D 473/32
[52] U.S. Cl. .................................... 544/276; 544/251; 544/277
[58] Field of Search ........................ 544/276, 277, 251

[56] References Cited

U.S. PATENT DOCUMENTS

| | | | |
|---|---|---|---|
| 4,728,736 | 3/1988 | Shealy et al. | 544/254 |
| 4,783,532 | 11/1988 | Kaneko et al. | 544/277 |
| 4,954,504 | 9/1990 | Chen et al. | 514/265 |

FOREIGN PATENT DOCUMENTS 0345076 12/1989 European Pat. Off. .
3901502 7/1989 Fed. Rep. of Germany .

OTHER PUBLICATIONS

Ueda, et al., Chemical Abstracts, vol. 86: 5767r (1977).
Kikkoman Shoyu Co., Ltd., Chemical Abstracts, vol. 94: 140122g (1981).
Ueda et al., *Chem. Pharm. Bull.*, 26(7), 2122-2127 (1978).
Miura et al, *Chem. Pharm. Bull.*, 23(2), 464-466 (1975).
Biggadike et al., *J. Chem. Soc. Chem. Commun.*, 14, 1083-1084 (1987).
Shealy et al, *J. Med. Chem.*, 27, 670-674 (1984).
Shealy et al, *J. Pharm. Sci.*, 62(9), 1432-1434 (1973).

*Primary Examiner*—Diana Rivers
*Attorney, Agent, or Firm*—Bacon & Thomas

[57] ABSTRACT

A process is described for the preparation of carbocyclic guanosine from aristeromycin in a multi-step procedure, the final step of which is the hydrolysis of a compound of the formula

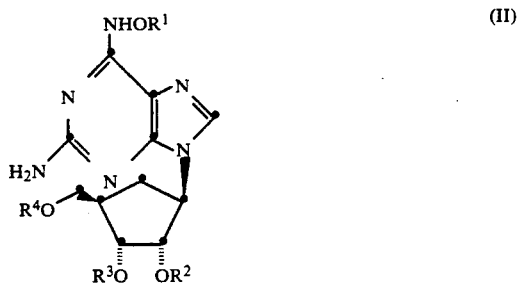

(II)

wherein $R^1$ represents a $C_{1-6}$alkyl group or an aryl$C_{1-4}$alkyl group and $R^2$, $R^3$ and $R^4$ each independently represent a hydrogen atom or a hydroxyl protecting group.

Carbocyclic guanosine is an intermediate in the synthesis of carbocyclic analogues of nucleosides having use in therapy, particularly as antiviral agents.

8 Claims, No Drawings

PROCESS FOR THE PREPARATION OF A CARBOCYCLIC NUCLEOSIDE ANALOGUE

This invention relates to a new process for the preparation of carbocyclic guanosine. More particularly, the invention describes the conversion of the natural product aristeromycin to carbocyclic guanosine utilising an improved multistep synthesis.

In the sugar series the chemical conversion of the base adenine to guanine has been achieved in a seven step sequence as reported by K. Ueda et. al. in *Chem. Pharm. Bull.* 23(2), 464–466 (1975) and in *Chem. Pharm. Bull.* 26(7), 2122–2127 (1978). The final two steps in the K. Ueda process for preparing guanosine from adenosine are as follows:

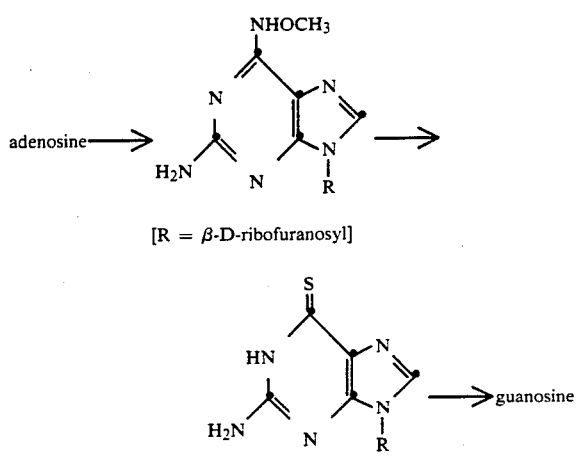

[R = β-D-ribofuranosyl]

The conversion of the Z-amino-6-alkoxyamino-9H-purine base to the 6-thioguanine base in the K. Ueda process is carried out under forcing conditions (sealed tube at an elevated temperature) In the presence of the very toxic reagent liquid hydrogen sulphide.

We have now found that in the carbocyclic series the conversion of the 2-amino-6-alkoxyamino-9H-purine base to guanine, thus providing carbocyclic guanosine, can be effected in a single step under relatively mild conditions and avoids the use of hydrogen sulphide. The present Invention thus provides in a first aspect a process for the preparation of carbocyclic guanosine a compound of formula (I)

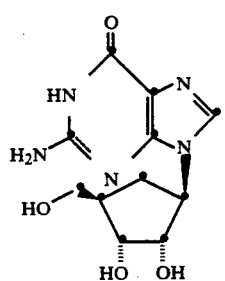

(I)

which comprises hydrolysing a compound of formula (II)

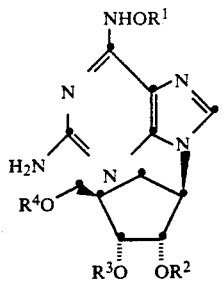

(II)

wherein $R^1$ represents a $C_{1-6}$alkyl group or an aryl$C_{1-4}$alkyl group and $R^2$, $R^3$ and $R^4$ each independently represent a hydrogen atom or a hydroxyl protecting group, followed, where necessary, by removal of any protecting groups present.

The hydrolysis may conveniently be effected in the presence of a suitable acid such as an inorganic acid (e.g. hydrochloric acid, nitric acid or sulphuric acid) at a temperature in the range of $-10°$ C. to $+120°$ C., for example at 80° to 120° C. and in a solvent such as water or a mixture of water and a water-miscible solvent such as an alcohol (e.g. methanol or ethanol), an ether (e.g. dioxane or tetrahydrofuran), a ketone (e.g. acetone), an amide (e.g. dimethylformamide) or a sulphoxide (e.g. dimethylsulphoxide). In some cases the acid may also be used as the reaction solvent, especially when the acid is hydrochloric acid.

When $R^1$ represents a $C_{1-6}$alkyl group this may be a straight chain or branched chain alkyl group such as methyl, ethyl, n-propyl, i-propyl, n-butyl, i-butyl or t-butyl and is preferably methyl. When $R^1$ represents an aryl$C_{1-4}$alkyl group the term 'aryl' preferably means phenyl and the $C_{1-4}$alkyl portion may be a straight chain or branched chain alkyl group, when $R^1$ is an aryl$C_{1-4}$alkyl group $R^1$ is preferably benzyl.

$R^2$ may represent any suitable hydroxyl protecting group which may be introduced and removed without affecting the rest of the molecule. Suitable hydroxyl protecting groups will be familiar to those skilled in the art and may include groups disclosed in 'Protective Groups in Organic Chemistry', Ed. J. F. W. McOmie (Plenum Press, 1973) and 'Protective Groups in Organic Synthesis' by T. W. Greene (John Wiley and Sons, 1981). Examples of suitable hydroxyl protecting groups include silyl groups such as trialkylsilyl (e.g. t-butyldimethylsilyl or thexyldimethylsilyl) and acyl groups (e.g. acetyl). The aforementioned silyl and acyl groups may be removed under the hydrolysing conditions described above.

Compounds of formula (II) may be prepared from compounds of formula (III)

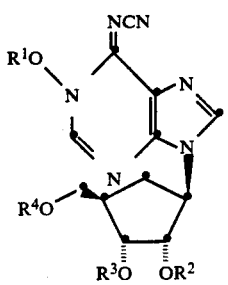

(III)

(wherein $R^1$ to $R^4$ are as defined above) by heating the compound (III), e.g. at reflux, in a suitable solvent such as an alcohol (e.g. ethanol) conveniently also containing some water, and in the presence of a suitable base such as an organic base (e.g. 1,8-diazabicyclo[5.4.0]undec-7-ene) or an inorganic base such as an alkali or alkaline earth metal carbonate (e.g. sodium bicarbonate or potassium bicarbonate).

Compounds of formula (III) in which one or more of $R^2$-$R^4$ represents a hydroxyl protecting group may be prepared from compounds of formula (III) in which $R^2$-$R^4$ represent hydrogen atoms by introduction of the hydroxyl protecting groups) using conventional means. Thus, For example, allyl groups may be introduced by treating the appropriate compound of formula (III) with a silyl halide such as a trialkylsilyl halide (e.g. a t-butyldimethylsilyl halide or a thexyldimethylsilyl halide) in a suitable solvent such as an aprotic dipolar solvent (e.g. dimethylformamide) conveniently in the presence of a suitable base such as an organic base (e.g. imidazole or triethylamine). The reaction may conveniently be carried out at ambient temperature. Acyl groups may conveniently be introduced by treating the appropriate compound of formula (III) with an acylating agent, such as for example a carboxylic acid anhydride (e.g. acetic anhydride) in the presence of a base, for example an organic base such as a trialkylamine (e.g. triethylamine) or dimethylaminopyridine or s mixture of such bases. The reaction may conveniently be effected in a suitable solvent such as an amide (e.g. dimethylformamide) at about ambient temperature.

Compounds of formula (III) In which $R^2$-$R^4$ represent hydrogen atoms may be prepared from a compound of formula (IV)

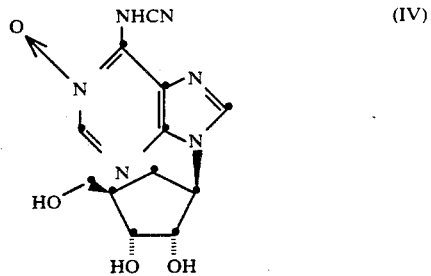

(IV)

by treating the compound (IV) with a suitable alkylating agent or aralkylating agent, e.g. a reagent $R^2X$ or $(R^2O)_2SO_2$ where $R^2$ is as defined above and X Is a halogen atom such as iodine.

The compound of formula (IV) may ba prepared by treating a compound of formula (V)

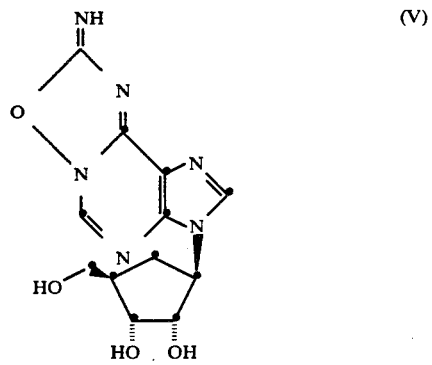

(V)

or a salt thereof (e.g. the hydrobromide) with a suitable base such as a tertiary amine (e.g. triethylamine) in a solvent such as an aprotic dipolar solvent (e.g. dimethylformamide) conveniently at ambient temperature.

The compound of formula (V) may be prepared by treating a compound of formula (VI)

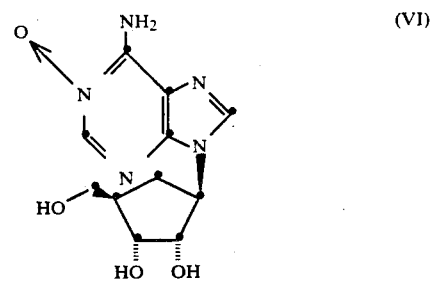

(VI)

with cyanogen bromide in a solvent such as an alcohol (e.g. methanol) or an aprotic dipolar solvent such as an amide (e.g. dimethylformaide) at a temperature conveniently within the range of $-50°$ C. to $+50°$ C., for example at about ambient temperature.

The compound of formula (VI) may be p by oxidising aristeromycin, a compound of formula (VII)

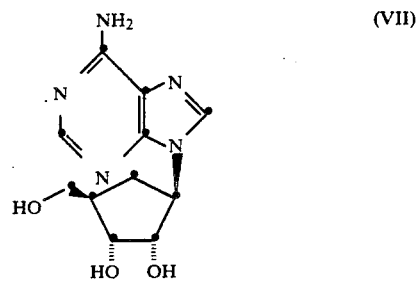

(VII)

The oxidation may conveniently be effected using a peracid such as m-chloroperoxybenzoic acid or peracetic acid (preferably containing a small amount of sodium acetate). The reaction using m-chloroperoxybenzoic acid may conveniently be effected in a suitable solvent such as a halogenated hydrocarbon (e.g. chloroform) at ambient temperature. The reaction using peracetic acid may conveniently be effected in a solvent such as a ketone (e.g. acetone), preferably also containing water, at ambient temperature.

It will be appreciated that certain of the above mentioned steps may be combined. In particular, compounds of formula (III) may be prepared from compound (V) via the compound (IV) in a 'one-pot' reaction. Similarly, compounds of formula (III) may be prepared from the compound of formula (VI) via the compounds (V) and (IV) in a 'one-pot' reaction. The compound of formula (I) may also be prepared from compounds of formula (III) via compounds (II) by a sequential combination of the reaction conditions described above.

Compounds of formulae (II) to (VI) are novel intermediates and represents further aspects of the present invention. Compounds of formula (II) are key intermediates and represent a particular aspect of this invention.

It is to be understood that each of the individual steps in the multistep process herein for preparing carbocyclic guanosine from aristeromycin and sequential combinations of such steps represent particular aspects of the present invention.

Carbocyclic guanosine is a known compound which is particularly useful as an intermediate in the synthesis of carbocyclic analogues of nucleosides having use in therapy, particularly as antiviral agents.

Aristeromycin is a known compound which may be isolated from *Streptomyces citricolor* IFO 13005 B-16575 and described by T. Kusaka et at. in *Journal of Antibiotices* 21, 255-263 (1968).

The following examples illustrate the present invention but are not intended to limit the present invention in any way.

EXAMPLE 1

[1′R,2′S,3′R,4′R]-2-Amino-1,9-dihydro-9-[2,3-dihydroxy-4-(hydroxymethyl)-1-cyclopentyl]-6H-purin-6-one (a)

[1R,2S,3R,5R]-3-(6-Amino-9H-purin-9-yl)-5-(hydroxymethyl)-1,2-cyclopentanediol,1-oxide (—)Ariateromycin[1] (4.0 g) was dissolved in a mixture of water (120 ml) and dioxane (120 ml). m-Chloroperbenzoic acid (5.20 g) was added. The mixture was stirred in the dark for 68 hours, and the solvent was removed and azeotroped several times with ethanol. The solid residue was triturated with diethyl ether, dried and recrystallised from methanol (120 ml). The solid was collected, washed with methanol and then diethyl ether and dried to give the title compound (3.53 g); m.p. 145°-149° C. (dec).

1. Journal of the American Chemical Society 1983, vol. 105, 4049-4055.

(b)

[1S,2R,3R,5R]-3-(Hydroxymethyl)-5-(2-imino-2,7-dihydro[1,2,4]oxadiazolo[3,2-i]purin-7-yl)-1,2-cyclopenianediol, hydrobromide A suspension of the title product of part (a) above (5.00 g) in methanol (300 ml) was stirred at −20° C. and a solution of cyanogen bromide (2.02 g) in methanol (100 ml) was added slowly over a period of 15 minutes at such a rate that the internal temperature was below −10° C. The reaction temperature was allowed to rise gradually to 10° C., over a period of 3 h. After stirring for 3 h, the solvent was removed to leave a white solid which was triturated with diethyl ether and filtered. The white solid was dried in vacuo to give the title compound (6.39 g). A portion of the solid (500 mg) was dissolved in methanol (23 ml) and ethyl acetate (60 ml) was added. The resulting solid was stored in the fridge overnight and then filtered. The off-white solid was dried in vacuo at 50° C. to give the title compound (292 mg); m.p. 180°-1840° C. (dec).

(c)

[1″R,2″S,3″R,4″R]-1-[9-(2,3-Dihydroxy-4-(hydroxymethyl)-cyclopentyl)-9H-purin-6-yl]-cyanamide,1′-oxide The title product of part (b) above (5.84 g) was dissolved in methanol (280 ml) and then saturated ammonia in methanol (58 ml) was added. The light yellow solution was left standing at room temperature for 1 hour. Evaporation of the solution under reduced pressure to a half of the volume gave a precipitate. This was stored in the refrigerator overnight and then the solid was filtered washed with a mixture of methanol and diethyl ether (1:1) to give a first crop of the title compound as a very pale yellow solid (1.44 g); m.p. 114°-118° C. (dec).

(d)

[1″R,2′S,3″R,4″R]-1-]1,9-Dihydro-1-methoxy-9-(2,3-dihydroxy-4-(hydroxymethyl)-1-cyclopentyl)-6H-purin-6-ylidene]-cyanamide The title product of part (c) above 13.76 g) was partially dissolved in dimethylformamide (47.6 ml), stirred in a water-bath and triethylamine (2.9 ml) was added. To the mixture was added iodomethane (3.0 ml). After stirring at room temperature for 3 hours, the resulting solution was evaporated under reduced pressure to leave a gummy residue which was dissolved in water (20 ml) and applied onto an XAD-2 column (150 g), eluting successively with water (1L) 5% methanol (1L), 10% methanol (1L), 20% methanol (1L), 30methanol (IL) and 50% methanol (1L). The appropriate fractions were separated and evaporated to give the title compound (1.91 g); m.p. 108°-110° C.

(e)

[1R,2S,3R,5R]-3-[2-Amino-6-(methoxyamino)-9H-purin-9-yl]-5-(hydroxymethyl)-1,2-cyclopentanediol The title product of part (d) (739 mg) was dissolved in 1.0N sodium hydroxide (46.2 ml) and stirred at room temperature for 2 hours. Dowex 50 (H+) was then added until the pH was 7. The resin was filtered off and to the filtrate was added ethanol (50 ml). The resulting light yellow mixture was heated in an oil-bath at 87° C. for 3 hours and evaporated to dryness to leave a brown solid residue. A portion of this solid (100 mg) was dissolved in ca. 2 ml of methanol and applied to a slurry silica gel column (12 g), eluting with mixtures of acetone and water (15:1, 300 ml) and (5:1, 120 ml). The appropriate fractions were separated and evaporated to give the title compound as a pale yellow solid (51 mg); m.p. 106°-110° C.

(f)

[1′R,2′S,3′R,4′R]-2-Amino-1,9-dihydro-9-[2,3-dihydroxy-4-(hydroxymethyl)-1-cyclopentyl]-6H-purin-6-one A solution of the title product of part (e) above (500 mg) in 6N hydrochloric acid (40 ml) was refluxed (oil-bath temperature 125° C.) for 3 hours. After cooling to room temperature, the solvent was removed under reduced pressure to leave a dark brown foam which was dried in vacuo. This was dissolved in water (2 ml) and the pH was adjusted to pH 7 by the addition of saturated sodium bicarbonate solution. The grey precipitate formed was filtered washed with water ethanol and then diethyl ether, and dried to give the title compound (95 mg); m.p. 292°-295° C.

The mother liquor was concentrated (to ca. 2 ml) and the resulting precipitate filtered, washed with water ethanol and then diethyl ether and dried to give a further quantity of the title compound (52 mg); m.p. 292°-295° C.

EXAMPLE 2

[1′R,2′S,3′R,4′R]-2-Amino-1,9-dihydro-9-[2,3-dihydroxy-4-(hydroxymethyl)-1-cyclopentyl]-6H-purin-6-one (a)

[1R,2S,3R,5R]-3-(6-Amino-9H-purin-9-yl)-5-(hydroxymethyl)-1,2-cyclopentanediol,1-oxide (−)Aristeromycin (20.0 g) was stirred overnight at room temperature with anhydrous sodium acetate (3.2 g) and 40% peracetic acid (40 ml) in acetone-water (3:1, 400 ml). The mixture was diluted with acetone 1400ml) and after 1 hour the solid was harvested, washed with acetone-water (10:1) and acetone and dried in vacuo at 40° C. The mother liquor and washes were combined and evaporated to ca. 300 ml and the dried solid was added. The mixture was stirred for 30 minutes, diluted with acetone (400 ml) and the product harvested after 30 minutes. This was washed with acetone-water (10:1) and acetone and dried to give the title compound (18.5 g); $^1$H n.m.r. DMSO-d$_6$) 8.60 ($^1$H), 8.36 (1H), 9.0–7.5 (2H), 4.74 (1H), 4.34 (1H), 3.89 (1H), 5.0–4.2 (3H), 3.65–3.4 (2H), 2.32 (1H), 2.10 (1H), 1.78 (1H); $\lambda_{max}$ (methanol) 234 nm (E⊥1284), 263 (E⊥250).

(b)

[1S,2R,3R,5R]-3-(hydroxymethol)-5-(2-imino-2,7-dihydro[1,2,4]-oxadiozolo[3,2-i]purin-7yl)-1,2-cyclopentanediol, hydrobromide A slurry of the title product of part (a) above (65.8 g) in methanol (1.3L) at 7° C. was treated with cyanogen bromide (27.8 g). The mixture was stirred at ca. 10° C. for 1 hour. Ethyl acetate was then added over 1½ hours and stirring was continued for 45 minutes. The solid was filtered off, washed with ethyl acetate and dried in vacuo at 40° to give the title compound (80.2 g); $^1$H n.m.r. (DMSO-d$_6$) 10.02 (1H), 8.94 (1H), 11.2–9.8 (2H), 4.98 (1H), 4.40 (1H), 3.93 (1H), 3.6–3.4 (2H), 2.39 (1H), 2.16 (1H), 1.81 (1H); $\lambda_{max}$ methanol) 227 (E⊥665), 283 (E⊥513).

(c)

[1″R,2″S,3″R,4″R]-1[1,9-Dihydro-1-methoxy-9-(2,3-dihydroxy-4-((thexyldimethylsilyloxy)methyl)-1-cyclopentyl)6H-purin-6-ylidene]-cyanamide A slurry of the title product of part (b) above (5 g) in dimethylformamide (25 ml) was treated with triethylamine (5.0 ml). The mixture was cooled and stirred at ca. 15° C. for 30 minutes, cooled to 10° C. and treated with iodomethane (2.5 ml). After 4.25 hours at room temperature more iodomethane (0.5 ml) and triethylamine (1 ml) were added and the mixture was left to stand for 20 minutes.

The reaction mixture was cooled to 15° C. and treated with more triethylamine (5 ml) and thexyldimethylsilyl chloride (3.2 ml). The mixture was left overnight, then partitioned between ethyl acetate (100 ml) and water (100 ml). The aqueous phase was reextracted with ethyl acetate (100 ml) and the organic layers washed with 2% sodium chloride solution, combined and evaporated to an orange syrup. Crystallisation from ethyl acetate (12 ml) by portionwise addition of diisopropyl ether (60 ml) with seeding gave, after 24 hours, a yellow solid which was harvested, washed with diisopropyl ether - ethyl acetate (5:1) and diisopropyl ether and dried to give the title compound (2.8 g); $^1$H n.m.r. (DMSO-d$_6$) 8.85 (1H), 8.41 (1H), 5.02 (1H), 4.76 (1H), 4.72 (1H), 4.30 (1H), 4.13 (1H), 3.85 (1H), 3.8–3.55 (2H), 2.28 (1H), 2.12 (1H), 1.72 (1H), 1.62 (1H), 0.90 (6H), 0.86 (6H), 0.13 (6H); $\lambda_{max}$ (methanol) 287 (E⊥408).

(d)

[1R,2S,3R,5R]-3-[2-Amino-6-(methoxyamino)-9H-purin-9yl]-5-((thexyldimethylsilyloxy)methyl)-1 2-cyclopentanediol 1,8-Diazabicyclo[5.4.0]undec-7-ene (0.65 ml) was added to a slurry of the title product of part (c) above (2 g) in a mixture of industrial methylated spirit (20 ml) and water (25 ml). The mixture was refluxed for 1 hour, cooled and evaporated to give an oil. This was partitioned between ethyl acetate (25 ml) and water (25 ml) and the ethyl acetate layer was washed with water and the water layers backwashed with ethyl acetate. The organic layers were evaporated to a small volume and the residue redissolved in ethyl acetate to provide a thick slurry. Diisopropyl ether (1 volume) was added slowly and the resulting solid was filtered off, washed with diisopropyl ether-ethyl acetate (1:1), then with diisopropyl ether and dried at 40° C. in vacuo to give the title compound (1.65 g); $^1$H n.m.r. (DMSO-d$_6$) 9.73 (1H), 7.52 (1H), 6.43 (2H), 4.93 (1H), 4.7–4.3 (2H), 4.16 (1H), 3.75 (3H), 3.7 (1H), 3.62 (2H), 2.22 (1H), 2.03 (1H), 1.7–1.3 (2H), 0.88 (6H), 0.85 (6H), 0.07 (6H); $\lambda_{max}$ (methanol) 281 nm (E⊥321).

(e)

[1′R,2′S,3′R,4′R]-2-Amino-1,9-dihydro-9-[2,3-dihydroxy-4-(hydroxymethyl)-1-cyclopentyl]-6H-purin-6-one A solution of the title product of part (d) above (2 g) in 6M hydrochloric acid (20 ml) was heated at 95° C. overnight. The mixture was evaporated to a syrup. Water (25 ml) was added and the mixture reevaporated. The resulting syrup was stirred with acetone (2 ml) and water (10 ml) and triethylamine 12 ml) were added. The mixture was cooled in ice for 30 minutes and the solid formed was filtered off, washed with a mixture of acetone (13 ml) and water (5 ml) and dried in vacuo at 40° C. to give the title compound (0.65 g); $^1$H n.m.r. (DMSO-d$_6$) 10.52 (1H) 7.79 (1H) 6.36 (2H) 5.0–4.4 (3H), 4.56 (1H) 4.22 (1H) 3.84 (1H), 3.6–3.35 (2H), 2.22 (1H), 2.02 (1H), 1.54 (1H); $\lambda_{max}$ methanol) 255 nm (E⊥373), 280 nm (E⊥252).

EXAMPLE 3

[1′R,2′S,3′R,4′R]-2-Amino-1,9-dihydro-9-[2,3-dihydroxy-4-(hydroxymethl)-1-cyclopentyl]-6H-purin-6-one (a)

[1″R,2″S,3″S,3″R]-1-[1,9-Dihydro-1-methoxy-9-(2,3-diacetoxy-4-(acetoxymethyl)-1-cyclopentyl)-6H-purin-6-ylidene]-cyanamide (i) The title product of Example 2, part (b) above (12.4 g) in dimethylformamide (50 ml) was treated with triethylamine (12.5 ml) and the mixture stirred at ambient temperature for 30 minutes. Dimethyl sulphate (10 ml) was added with the temperature kept below 28° C. After 30 minutes, more triethylamine (4.1 ml) was added. The mixture was recooled to 23° C. and more dimethyl sulphate (3.2 ml) was added. After 30 minutes the mixture was treated with dimethylaminopyridine (0.1 g), followed by triethylamine (24 ml), cooled in a chilled water bath and treated with acetic anhydride (14 ml) added cautiously. The mixture was stirred at ambient temperature for 1½ hours. Chilled water (70 ml) was added slowly with stirring followed by more water (130 ml) added dropwise to give a slurry. This was cooled in ice for 1 hour and the solid was filtered off, washed with water and dried in vacuo at 50° C. to give the title compound (10.17 g); $^1$H n.m.r. (DMSO-d$_6$) 8.92 (1H), 8.54 (1H), 5.62 (1H), 5.26 (1H), 5.12 (1H), 4.4–4.0 (2H), 4.14 (3H), 2.7–2.35 (2H), 2.2–2.0 (1H), 2.10 (3H), 2.08 (3H), 1.95 (3H); $\lambda_{max}$ (methanol) 286 nm (E⊥437).

(ii) To a solution of cyanogen bromide (8.5 g) in dimethylformamide (100ml) was added the title product of Example 2, part (a) above (20 g) over 5 minutes. The mixture was stirred for 1½ hours and triethylamine (33 ml) was added. Stirring was continued for 30 minutes and dimethyl sulphate (20 ml) was added over 15 minutes with cooling. Stirring was continued for a further 1 hour and more dimethyl sulphate (3.5 ml) was added. After 20 minutes more dimethyl sulphate (1.75 ml) was added and after a further 20 minutes more triethylamine (48 ml) and dimethylaminopyridine (0.2 g) were added. The mixture was treated with acetic anhydride (28 ml) over 10 minutes with the temperature kept below 28±4° C. and stirred for 30 minutes. Iced water (400 ml) was added and the mixture stirred at ambient temperature overnight. The yellow crystalline solid was filtered off, washed with water and dried in vacuo at 50° C. to give the title compound (17.6 g); $^1$H n.m.r. data are as in part (i) above.

(b)
[1′R,2′S,3′R,4′R]-2-Amino-1,9-dihydro-9-[2,3-dihydroxy-4-(hydroxymethyl)-1-cyclopentyl]-6H-purin-6-one (i) The title product of Example 3(a)(ii) (53.2 g) was slurried in a mixture of industrial methylated spirit (450 ml) and water (50 ml). 1,8-Diazabicyclo[5.4.0]undec-7-ene (18 ml) was added and the mixture was heated at reflux for 1½ hours. The mixture was then evaporated to a dark oil. The oil was heated in 6M hydrochloric acid (300 ml) on a steam bath overnight and then concentrated to a dark oil by rotary evaporation. This oil was dissolved in a mixture of industrial methylated spirit (250 ml) and water (40 ml). The mixture was stirred and treated with triethylamine (56 ml). The resulting solid was filtered off, washed with a mixture of industrial methylated spirit (125 ml) and water (20 ml) and dried. This was then dissolved in hot (85° to 90° C.) water(500 ml) and allowed to cool slowly. The mixture was then cooled to 10° C. and the solid filtered off, washed with water and industrial methylated spirit and dried to give the title compound (19.7 g); $^1$H n.m.r. (DMSO-d$_6$) 10.43 (1H), 7.75 (1H), 6.28 (2H), 5.0–4.2 (3H), 4.56 (1H), 4.23 (1H), 3.85 (1H), 3.6–3.4 (2H), 2.24 (1H), 2.05 (1H), 1.58 (1H) $\lambda_{max}$(methanol) 255 nm (E⊥368), 280 nm (E⊥247).

(ii) The title product of Example 3(a)(ii) (37.5 g) was refluxed with saturated sodium bicarbonate solution (37.5 ml) in industrial methylated spirit (375 ml) for 1.7 hours. The solution was then evaporated to a syrup which was heated overnight on a steam bath with added 5M hydrochloric acid (75 ml). The mixture was then treated with 3H sodium hydroxide (200 ml) followed by concentrated hydrochloric acid (ca. 10 ml) until the pH was 5. The mixture was cooled to 5° C. for 1 hour and the solid harvested, washed with water and dried to give the title compound (15.8 g); $^1$H n.m.r. data are as in part (i) above; $\lambda_{max}$ (methanol) 255 nm (E⊥377) 280 nm (E⊥256).

(iii) The title product of Example 3(a)(ii) (5.0 g) was added to a solution of potassium carbonate (0.77 g) in water (5 ml) and industrial methylated spirit (50 ml). The mixture was refluxed for 1 hour, allowed to cool to room temperature and allowed to stand for 3 hours. The solution was then evaporated to a syrup which was treated with 5M hydrochloric acid and refluxed for 20 hours. Acetone was then added and the pH adjusted to ca. 6 with 3M sodium hydroxide (12 ml). The mixture was then stirred and heated to 80° C. and water (5 ml) was added with the temperature kept at 80±4° C. for a further 15 minutes. The mixture was allowed to cool to room temperature and cooled and stirred at 5° C. for 1 hour. The solid was harvested, washed with water and industrial methylated spirit and dried in vacuo to give the title compound (2.27 g); $^1$H n.m.r. data are as in part (i) above; $\lambda_{max}$ (methanol) 255 nm (E⊥359) 280 nm (E⊥244).

We claim:

1. Process for the preparation of a compound of formula (I)

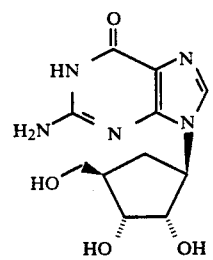

(I)

which comprises hydrolysing a compound of formula (II)

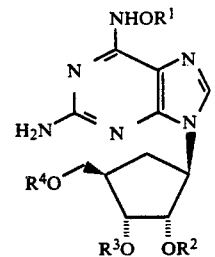

(II)

wherein R$^1$ represents a C$_{1-6}$alkyl group or an arylC$_{1-4}$alkyl group and R$^2$, R$^3$ and R$^4$ each independently represent a hydrogen atom or a hydroxyl protecting group, followed, where necessary, by removal of any protecting groups present, and wherein the hydrolysis is effected at a temperature in the range of −10° C. to +120° C. in the presence of inorganic acid.

2. Process according to claim 1 wherein a compound of formula (II) is prepared by heating a compound of formula (III)

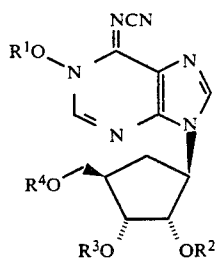

(III)

in which $R^1$-$R^4$ are as defined in claim 1.

3. Process according to claim 2 in which a compound of formula (III) is heated in the presence of an organic or inorganic base in a solvent to provide a compound of formula (II).

4. Process according to claim 1 in which $R^1$ represents a $C_{1-6}$alkyl group.

5. Process according to claim 1 in which $R^1$ represents a methyl group.

6. Process according to claim 1 in which $R^2$, $R^3$ $R^4$ represent acyl groups.

7. Process according to claim 1 in which $R^2$, $R^3$ and $R^4$ represent acetyl groups.

8. Process according to claim 1 in which the inorganic acid is hydrochloric acid.

* * * * *